United States Patent [19]

Tsuji et al.

[11] Patent Number: 4,532,233
[45] Date of Patent: Jul. 30, 1985

[54] FLUOROMETHYLTHIOOXACEPHALOSPORINS

[75] Inventors: Teruji Tsuji, Osaka; Hisao Sato, Nara; Yoshio Hamashima, Kyoto, all of Japan

[73] Assignee: Shionogi & Co., Ltd., Osaka, Japan

[21] Appl. No.: 564,553

[22] Filed: Dec. 22, 1983

[30] Foreign Application Priority Data

Dec. 23, 1982 [JP] Japan ................. 57-234472

[51] Int. Cl.³ ................. A01N 43/90; C07D 498/04
[52] U.S. Cl. ................. 514/63; 514/186; 514/191; 514/210; 544/64; 544/69; 544/90
[58] Field of Search ................. 544/69, 90, 64; 424/248.52, 184, 245

[56] References Cited

U.S. PATENT DOCUMENTS 4,232,151 11/1980 Nagata et al. ................. 544/90
4,371,532 2/1983 Narisada et al. ................. 424/248.51

Primary Examiner—Richard L. Raymond
Attorney, Agent, or Firm—Wenderoth, Lind & Ponack

[57] ABSTRACT

An antibacterial 7β-(fluorinated methylthioacetamido)-7α-methoxy-3-(1-hydroxyalkyl-5-tetrazolyl)thiomethyl-1-dethia-1-oxa-3-cephem-4-carboxylic acid and its derivatives at the carboxy or hydroxyalkyl represented by the following formula:

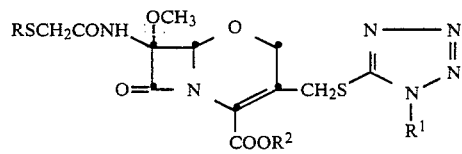

wherein, R is $FCH_2-$ or $F_2CH-$; $R^1$ is $R^3O$-substituted-alkyl in which $R^3$ is hydrogen or a hydroxy-protecting group; and $R^2$ is a hydrogen or light metal atom or a carboxy-protecting group, antibacterial drugs containing it, its use and production.

9 Claims, No Drawings

FLUOROMETHYLTHIOOXACEPHALOSPORINS

This invention relates to new antibacterials, 7β-(fluorinated methylthioacetamido)-7α-methoxy-3-(1-hydroxyalkyl-5-tetrazolyl)thiomethyl-1-dethia-1-oxa-3-cephem-4-carboxylic acids and their derivatives of the following formula:

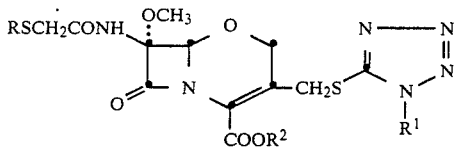

wherein,

R is $FCH_2-$ or $F_2CH-$;

$R^1$ is $R^3O$-substituted-alkyl, in which $R^3$ is hydrogen or a hydroxy-protecting group; and $R^2$ is a hydrogen or light metal atom or a carboxy-protecting group.

In the above formula (I), the hydroxyalkyl represented by $R^1$ can be hydroxyethyl, hydroxypropyl, hydroxyisopropyl, or the like. The protecting group $R^3$ of this hydroxyalkyl can contain 1 to 12 carbon atoms and form an aliphatic acid ester (e.g., chloroacetate, dichloroacetate), carbonate ester (e.g., butoxyformate, benzyloxyformate, alkylbenzyloxyformate), alkanoate ester (e.g. acetate, propionate, benzoate), alkoxyalkyl ether (e.g., methoxymethyl ether, ethoxyethyl ether, tetrahydrofuranyl ether, tetrahydropyranyl ether), alkyl ether (e.g., tert-butyl ether), aralkyl ether (e.g., diphenylmethyl ether), silyl ether (e.g., trimethylsilyl ether, dimethyl-t-butylsilyl ether), stannyl ether (e.g., trimethylstannyl ether), or other equivalent protecting group.

The carboxy-protecting group for Compound (I) can be a conventional carboxy derivative including, for example, an inorganic salt (e.g., lithium, sodium, potassium, magnesium, calcium, aluminum, or ammonium salt); organic base salt (alkylamine, e.g., ethylamine, diethylamine, triethylamine, piperidine, morpholine, aromatic amine, e.g., aniline, dimethylaniline, naphthylamine, aromatic base, e.g., pyridine, picoline, lutidine, quinoline, nicotinamide); 1 to 8C aliphatic ester (e.g., methyl, ethyl, propyl, isopropyl, butyl, isobutyl, t-butyl, hexyl ester), 7 to 15C aralkyl ester (e.g., benzyl, p-methylbenzyl, dimethylbenzyl, methoxybenzyl, nitrobenzyl, diphenylmethyl ester), 6 to 12C aromatic ester (e.g., phenyl, trichlorophenyl, diisopropylphenyl ester), 3 to 12C silyl ester (e.g., trimethylsilyl, dimethylmethoxysilyl ester), 3 to 12C stannyl ester (e.g., trimethylstannyl ester), acid anhydride (i.e., symmetric anhydride or unsymmetric anhydride with an inorganic acid, e.g., carbonic acid, sulfuric acid, phosphoric acid, sulfinic acid, or 1 to 12C organic acid as a carboxylic acid, e.g., acetic acid, propionic acid, valeric acid, benzoic acid, 1 to 12C sulfonic acid, e.g., methanesulfonic acid, ethanesulfonic acid, benzenesulfonic acid, mesitylenesulfonic acid, or the like), or an amide of an equivalent effect.

The light metal salt is a physiologically acceptable salt of the carboxy with a light metal atom of 1st to 3rd group, 2nd to 4th series of the Periodical Table, e.g., lithium, sodium, potassium, magnesium, calcium, aluminum.

The pharmacological esters of Compound (I) are oral or parenteral antibacterials, including substituted alkyl esters as 1-alkanoyloxyalkyl, e.g., acetoxymethyl, propionyloxyethyl, pivaloyloxymethyl; 3 to 6C alkoxyformyloxyalkyl, e.g., 1-ethoxycarbonyloxyethyl; and 4-methyl-2-oxo-1,3-dioxol-4-en-4-ylmethyl ester; 7 to 15C substituted aralkyl esters, e.g., phenacyl, phthalidyl ester; and 6 to 12C optionally substituted aryl esters, e.g., phenyl, xylyl, indanyl ester.

Compounds (I) show antibacterial effects on contacting with Gram-positive or Gram-negative bacteria. They are useful as bacterial growth inhibitors on human, animal, plant, or perishable objects, or as growth-promoting additives in human or animal feedstuffs. For example, they are useful for treating or preventing human, veterinary, or poultry infections caused by sensitive Gram-positive bacteria, e.g., *Bacillus cereus, Bacillus subtilis, Corynebacterium diphtheriae, Staphylococcus aureus, Streptococcus pyrogenes, Streptococcus pneumoniae*, or *enterococci*, or Gram-negative bacteria, e.g., *Enterobacter cloacae, Escherichia coli, Klebsiella pneumoniae, Proteus mirabilis, Proteus moganii, Proteus rettgeri, Proteus vulgaris, Salmonella paratyphi, Salmonella typhi, Seratia marsescens, Shigella sonnei*, or some anaerobic bacteria, e.g., *Bacteroides fragilis*.

Compounds (I) are also useful as starting materials for synthesizing other antibacterials.

Compounds (I) are useful in various oral or parenteral dosage forms solely or with other coacting substances. The pharmaceutical compositions contain 0.01 to 99% of Compound (I) dissolved, dispersed, or suspended in a solid or liquid pharmaceutical carrier. They are solid preparations, e.g., tablets, powder, dry syrups, troches, granules, capsules, pills, suppositories, or the like; or liquid preparations, e.g., injections, ointements, dispersions, inhalants, suspensions, solutions, emulsions, syrups, elixirs, or like. They can be flavored or colored, and tablets, granules, and capsules may be coated. They can be in a unit dosage form. The carriers are harmless to both Compound (I) and patients and include, for solids, binders, e.g., acacia, carboxymethylcellulose, gelatin, glucose, polyvinylpyrrolidone, sodium alginate, sorbitol, starch, syrups, tragacanth; bulking agents, e.g., bentonite, calcium carbonate, calcium phosphate, glycine, kaoline, lactose, salt, sorbitol, starch, sugar, talc; diluents, e.g., calcium carbonate, kaolin, lactose, starch, sucrose; disintegrators, e.g., agar, carbonates, sodium laurylsulfate, starch; lubricants, e.g., boric acid, cacao oil, magnesium stearate, paraffin, polyethylene glycol, silica, sodium benzoate, stearic acid, talc; or wetting agent; for solutions, solvents e.g., water, buffer, peanut oil, sesame oil, methyl oleate; emulsifying agents e.g. acacia, lethicin, sorbitan monooleate; suspending agents, e.g., carboxymethylcellulose, glucose, methyl cellulose, sorbitol, sugar syrup, gelatin, hydroxyethylcellulose, carboxymethylcellulose, aluminum stearate gel, hydrogenated fats; buffers; dispersing agents; or solubilizing agents; or for both, preservatives, e.g., methyl or ethyl p-hydroxybenzoate, sorbic acid; antioxidants; aromatic substances; analgesics; edible coloring agents; stabilizing agents; absorption promoters, e.g., glycerin mono or di-alkanoates; or the like.

Compounds (I) are stable and effective against bacteria resistant to other β-lactams. They have better characters, e.g., less Antabuse-like reaction, absorption, distriution, metabolism, excretion, etc. than other β-lactams. Usually, their doses are 10 μg to 1 mg topically or 1 to 2 g orally of the pharmaceutical esters or free acids, and 0.2 to 5 g of light metal salts or pharmaceutical esters intravenously or intramuscularly daily for preventing or treating bacterial infections. The dose and interval can be varied according to the sort of bacteria and seriousness of the disease.

Compound (I) are produced, e.g., as follows:
(1) Amidation.

Compound (I) can be produced by amidating the following Amine (II) or its reactive derivative with a fluorinated methylthioacetic acid (III) or its reactive derivative:

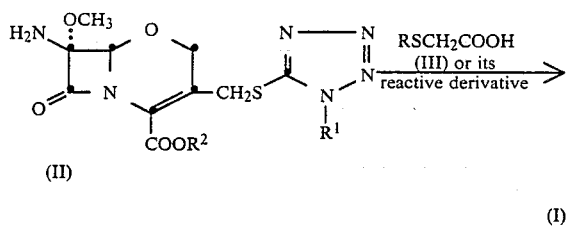

wherein, R, R¹, and R² are as defined above,

Amine (II) is preparable by the method of e.g., Japanese Patent Application Kokai No. 56-32993. The reactive derivative of Amine (II) has 7-amino activated by, e.g., silyl (e.g., trimethylsilyl, methoxydimethylsilyl), stannyl (e.g., trimethylstannyl), alkylene (a residue of enamino from, e.g., acetone, acetylacetone, acetoacetate, acetoacetonitrile, acetoacetanilide, cyclopentanedione, acetylbutanolide), alkylidene (e.g., 1-chloroethylidene, 1-chlorobenzylidene, 1-methoxyethylidene, 1-butoxy-1-phenoxyethylidene, propylidene, benzylidene), or acid (forming a salt of the amino with a mineral acid, e.g., hydrochloric acid, sulfuric acid; carboxylic acid, e.g., acetic acid, succinic acid; sulfonic acid, e.g., methanesulfonic, ethanesulfonic, benzenesulfonic acid); or the carboxy protected as referred to above.

The fluorinated methylthioacetic acid (III) are produced by reacting a fluoromethyl halide, an alcoholic alcoholate, and a thioglycolate, e.g., 1 to 8C alkyl ester. The reactive derivative of the acid (III) to be prepared in a conventional manner includes an acid anhydride, acid halide, reactive ester, reactive amide, azide, or the like.

The process of above acylation is as follows:

(a) Free acid (III)—One to two molar equivalents of Acid (III) is reacted with Amine (II) preferably in the presence of 1 to 2 molar equivalents of a condensing reagent (carbodiimide, e.g., N,N'-diethylcarbodiimide, N,N'-dicyclohexylcarbodiimide; carbonyl compound, e.g., carbonyldiimidazole; isoxazolinium salt; acylamino compound, e.g., 2-ethoxy-1-ethoxycarbonyl-1,2-dihydroquinoline; or the like) preferably in a nonprotic solvent, e.g., halohydrocarbon, nitrile, ether, amide, or the like solvent or a mixture thereof.

(b) Acid anhydride—This includes a symmetric anhydride, mixed anhydride (with mineral acid, e.g., phosphoric acid, sulfuric acid, carbonic half ester; 1 to 5C alkanoic acid, 7 to 12C aralkanoic acid, 1 to 12C sulfonic acid); and intramolecular anhydride, e.g., ketene, isocyanate. Preferably, Amine (II) or its reactive derivative is acylated with 1 to 2 molar equivalents of the acid anhydride in the presence of 1 to 10 molar equivalents of an acid scavenger (e.g., an inorganic base, e.g., oxide, hydroxide, carbonate, or hydrogen carbonate of alkali metal or alkaline earth metal; organic base, e.g., 3 to 12C tertiary amine, 4 to 12C aromatic base; 2 to 12C oxirane, e.g., alkylene oxide, aralkylene oxide; or the like), preferably in a nonprotic solvent, e.g., halohydrocarbon, nitrile, ether, amide, or the like solvent or a mixture thereof.

(c) Acid halide—This is chloride, bromide, or iodide. One to 2 molar equivalents of this acid halide is preferably reacted with Amine (II) or its reactive derivative in the presence of 1 to 10 molar equivalents of the acid scavenger of above (b), in a halohydrocarbon, nitrile, ether, ketone, water, dialkylamide, or the like solvent or their mixture.

(d) Reactive ester—This includes 2 to 6C enol ester, e.g., vinyl ester, isopropenyl ester; 6 to 12C aryl ester, e.g., chlorophenyl ester, nitrophenyl ester; heterocyclic ester, e.g., ester with 1-hydroxybenzotriazole; or ester with hydroxylamine or diacylhydroxylamine, and the like.

(e) Reactive amide—This is an aromatic amide, e.g., amide with imidazole, triazole, 2-ethoxy-1,2-dihydroquinoline, diacylanilide; or the like.

(f) Formimino compound—e.g., N,N-dimethylformimino ester. and (g) Other reactive derivatives.

The reactions from (d) to (g) are carried out by treating 1 molar equivalent of Amine (II) or its reactive derivative with 1 or more equivalents of the reactive derivative of fluorinated methylthioacetic acid (III) in a nonprotic solvent, e.g., halohydrocarbon, ether, ketone, amide, ester, or the like solvent or a mixture thereof.

(2) Introduction of the substituted tetrazolylthio

The objective Compound (I) or its derivative can be produced by treating a 1-dethia-1-oxacephem compound having 3-methyl substituted by a leaving group (IV) with Thiol (V) or its reactive derivative:

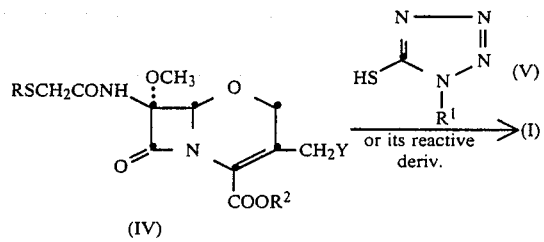

wherein Y is a leaving group replaceable with Thiocompound (V) and R, R¹, and R² are as defined above.

Halogen, phosphoryloxy, alkanesulfonyloxy, dichloroacetoxy, trichloroacetoxy or like acyloxy is representative of Y.

Salts of Compound (V) with alkali metal, e.g., sodium, potassium, magnesium, calcium; or organic base, e.g., triethylamine, are the representative reactive derivatives.

In this reaction, the starting material (IV) is brought to contact with Thiol compound (V), if required together with a base, preferably in an inert solvent, e.g., halohydrocarbon, ether, ketone, amide, or the like solvent.

(3) Methoxylation

Representative introduction of 7α-methoxy to the 7ξ-hydrogen-7ξ-(fluorinated methylthioacetamido)-3-substituted tetrazolyl-thiomethyl-1-dethia-1-oxa-3-cephem-4-carboxylic acid or its derivative is as follows:

(a) Reacting the 7-hydrogen compound with an N-halogenating reagent, e.g., t-butyl hypochlorite; alkali metal methoxide, e.g., sodium methylate, potassium methylate, and a reducing reagent in methanol.

(b) Reacting the 7ξ-hydrogen compound with t-butyl hypochlorite and methanol-base in a solvent, e.g., tetrahydrofuran, containing phenyllithium.

(5) Deprotection.

(i) Representative deprotections of protected carboxy to give the corresponding free carboxy are as follows:

(a) Highly reactive esters, amides, and anhydrides are hydrolyzed with water containing an acid, base, or buffer solution.

(b) Haloethyl, benzyl, nitrobenzyl, methylbenzyl, dimethylbenzyl, diphenylmethyl, triphenylmethyl, and the like esters give the free acid by hydrogenating over e.g., platinum, palladium, or nickel as catalyst; or mildly reducing with an acid and low valent metal, e.g., tin, zinc, divalent chromyl salt; or sodium dithionite.

(c) Benzyl, methoxybenzyl, methylbenzyl, dimethoxybenzyl, t-alkyl, trityl, diarylmethyl, cyclopropylmethyl, sulfonylethyl, cyclopropylethyl, and the like esters afford the free acid by solvolyzing with an acid, e.g., mineral acid, Lewis acid, sulfonic acid, strong carboxylic acid; if required in the presence of a cation scavenger, e.g., anisole.

(d) Phenacyl, ethynyl, p-hydroxy-3,5-di-t-butylbenzyl, and the like esters give the free acid with a base.

(ii) Representative deprotections of a hydroxy-protecting group giving the corresponding free hydroxy are as follows:

(a) Highly reactive ester-type protecting groups, e.g., haloalkanoyl, are removed with an aqueous base.

(b) Alkoxycarbonyl, aralkoxycarbonyl, t-butyl, t-alkylsilyl, and the like carbonate or ether-type protecting group can be removed with an acid, e.g., mineral acid, Lewis acid, strong carboxylic acid, at −50° C. to 50° C., optionally in the presence of a cation scavenger.

(c) Acetal, enol ether, trialkylsilyl, and the like ether type protecting groups are removed with an acid.

(6) Esterification

The carboxy in Compound (I) or its reactive derivative gives the corresponding ester with an alcohol or its reactive derivative. When esterified with alcohol, it requires a condensing reagent as cited for (1), (b) above. A mild and strong reagent is preferably used to avoid side reactions.

Reactive derivative of the alcohol can be a diazo compound or chloride, bromide, iodide, sulfonate, or the like to be used with an acid scavenger as (1), (b) above. Reactive carboxy derivatives include salts and mixed anhydrides with a carbonic acid, carboxylic acid, sulfonic acid, or mineral acid including hydrogen halides.

Esterifications can be one of those described in, e.g., J. F. W. McOmie Ed., "Protective Groups in Organic Chemistry", pp. 183 (1973), Plenum Press, N.Y.; S. Patai Ed., "The Chemistry of Carboxylic acids and Esters" in "The Chemistry of Functionsl Groups", pp 505 (1969), Interscience Publ., John Wiley & Sons, Ltd., London; and various patents.

(7) Salt formation

Compound (I) having free carboxy can form a salt by treating with an organic or inorganic base. The base can be a hydroxide or a salt of weak acid, e.g., weak carboxylic acid, carbonic acid, or the like. The separation of the salt from an organic solvent is preferable, as it is a simultaneous purification. Lyophilizing or concentrating a neutral aqueous solution may be used for isolation.

Said reactions proceed at between −50° C. and 100° C. over a 0.1 to 20 hours period, optionally in dry or stirred medium.

The reaction solvent is one of hydrocarbon, e.g., pentane, hexane, octane, benzene, toluene, xylene; halohydrocarbon, e.g., dichloromethane, chloroform, carbon tetrachloride, dichloroethane, trichloroethane, chlorobenzene; ether, e.g., diethyl ether, methyl isobutyl ether, dioxane, tetrahydrofuran; ketone, e.g., acetone, methyl ethyl ketone, cyclohexanone; ester, e.g., ethyl acetate, isobutyl acetate, methyl benzoate; nitrohydrocarbon, e.g., nitromethane, nitrobenzene; nitrile, e.g., acetonitrile, benzonitrile; amide, e.g., formamide, acetamide, dimethylformamide, dimethylacetamide, hexamethyl phosphorotriamide; sulfoxide, e.g., dimethyl sulfoxide; carboxylic acid, e.g., formic acid, acetic acid, propionic acid; organic base, e.g., diethylamine, triethylamine, pyridine, picoline, collidine, quinoline; alcohol, e.g., methanol, ethanol, propanol, hexanol, octanol, benzyl alcohol; water; ammonia; or other industrial solvent or a mixture thereof.

One obtains the product by removing impurities, e.g., unreacted starting materials, by-products, solvents; by e.g., concentrating, drying, evaporating, extracting, filtrating, precipitating, washing; and purifying by usual work up, e.g., adsorbing, chromatographying, distillating, eluting, lyophilizing, precipitating, crystallizing.

The compounds (I) are safer antibacterials than the structurally close compounds. For example, they have less side effects, e.g., disulfiram-like activity.

Test method: The test compound (1 g/kg each) was given to a group of 4 rats. After 18 hours ethanol (2 g/kg each) were given. After another 1 hour the rats were autopsied and the liver acetaldehyde dehydrogenase (ALDH) activity and the blood level of acetaldehyde (AC) were determined.

| | DISULFIRAM-LIKE ACTIVITY/ $R = F_2CH-$, $R^1 = CH_2CH_2OH$, $R^2 = H$ | |
|---|---|---|
| Test compound | Liver ALDH activity | Blood AC level |
| Control | 16.16 + 0.88 unit | 5.4 + 0.6 g/ml |
| Compound (I) | 13.81 + 1.20 | 3.5 + 0.9 |
| Disulfiram | 3.53 + 0.22 | 213.4 + 25.6 |

Following examples illustrate this invention.

In the Examples, "volume" shows milliliter for 1 gram of and "equivalent" shows molar equivalent for 1 molar equivalent of the starting beta-lactam. The product is usually isolated, if required after diluting with a solvent, e.g., dichloromethane, adjusting pH, washing with water, drying, and concentrating. Physicochemical constants are identical with that of the samples produced by other routes. In the examples, AOM is for acetoxymethyl, Cbz is for carbobenzoxy, ECE is for ethoxycarbonyloxyethyl, Ph is for phenyl, POM is for pivaloyloxymethyl, Tbz is for p-methylcarbobenzoxy, and THP is for tetrahydropyran-2-yl. Physical constansts are listed on Tables 1—1 to 2.

EXAMPLE 1

(Amidation)

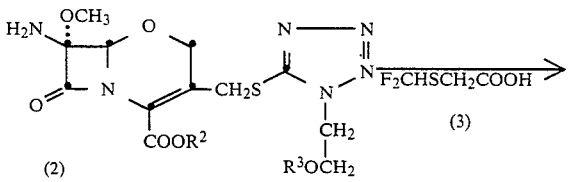

-continued

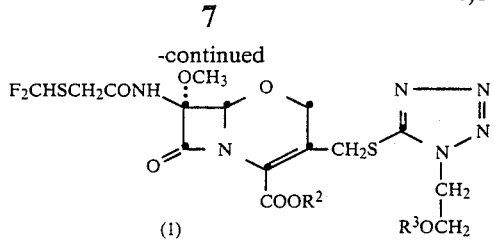

(1) $R^3 = PhCH_2OCO—$, $R^2 = CHPh_2$

To a solution of 7β-amino-7α-methoxy-3-[1-(2-benzyloxycarbonyloxyethyl)-1H-tetrazol-5-yl]thiomethyl-1-dethia-1-oxa-3-cephem-4-carboxylic acid diphenylmethyl ester (2 millimoles; IR(Nujol): 3340, 1785, 1758, 1720, 1632 cm$^{-1}$) in dichloromethane (1 to 3 volumes) are added pyridine or collidine (1 to 2 equivalents) and difluoromethylthioacetyl chloride (1.0 to 1.5 equivalents) at a temperature between −20° C. and 0° C., and the mixture is stirred for a 0.2 to 1 hour period. The reation mixture is diluted with ethyl acetate or dichloromethane, washed with brine or water and aqueous sodium hydrogen carbonate, dried and evaporated under reduced pressure. The residue is recrystallized from ethyl acetate to give 7β-difluoromethylthioacetamido-7α-methoxy-3-[1-(2-benzyloxycarbonyloxyethyl)-1H-tetrazol-5-yl]thiomethyl-1-dethia-1-oxa-3-cephem-4-carboxylic acid diphenylmethyl ester. Yield: 75%.

(2) In a manner similar to above, the following compounds are prepared from the corresponding 7β-amino-7α-methoxy-3-[1-(2-protected hydroxyethyl)-1H-tetrazol-5-yl]thiomethyl-1-dethia-1-oxa-3-cephem-4-carboxylic acid ester:

(a) $R^2 = t—C_4H_9$, $R^3 = t—C_4H_9$,
(b) $R^2 = POM$, $R^3 = H$,
(c) $R^2 = —CH_2C_6H_4OCH_3—p$, $R^3 = PhCH_2OCO—$,
(d) $R^2 = —CHPh_2$, $R^3 = H$, mp. 170°–172° C.
(e) $R^2 = —CHPh_2$, $R^3 = Cl_2CHCO—$,
(f) $R^2 = —CHPh_2$, $R^3 = PhCH_2OCO—$,
(g) $R^2 = —CHPh_2$, $R^3 = p—CH_3C_6H_4CH_2OCO—$,
(h) $R^2 = —CHPh_2$, $R^3 = $ tetrahydropyran-2-yl,
(j) $R^2 = —CHPh_2$, $R^3 = Si(CH_3)_2t—C_4H_9$, (3) The same products can be obtained by acylating under the following conditions:

(1) When COOR$^2$ of Amine (2) is carboxy, this is dissolved in aqueous (10 volumes) sodium hydrogen carbonate (2.5 equivalents) and the carboxylic acid (3) chloride (1.1 equivalent) is dropwise added thereto. The mixture is kept at a temperature between −5° C. and 40° C. over a 0.5 to 2 hours period.

(2) When COOR$^2$ is carboxy, the corresponding Amine (2) is treated with trimethylsilyl chloride and triethylamine (1.2 equivalents each) to O-silylate, and then treated with pyridine (4 equivalents) and the carboxylic acid (3) chloride (1.1 equivalents) at −30° C. over a 30 minutes to 2 hours period, and the obtained silyl ester is hydrolyzed with acid.

(3) A mixture of Amine (2), picoline (4 equivalents), trichloroethane, and the carboxylic acid (3) chloride (1.1 equivalent) is stirred at a temperature between 0° C. and −30° C. over a 30 minutes to 3 hours period.

(4) A mixture of Amine (2), dimethylformamide (2 volumes), ethyl acetate (10 volumes), triethylamine (1.1 equivalents), the carboxylic acid (3) chloride (1.2 equivalents), and dichloromethane (20 volumes) is stirred at a temperature between 0° C. and −30° C. over a 30 minutes to 2 hours period.

(5) A mixture of Amine (2), chloroform (10 volumes), dimethoxyethane (10 volumes), pyridine (1.5 moles), and a mixed anhydride of the carboxylic acid (3) and isobutoxyformic acid (1 to 2 equivalents) is stirred at a temperature between −5° and 10° C. over a 30 minutes to 6 hours period.

(6) A mixture of Amine (2), ethyl acetate (10 volumes), 1,2-dichloroethane (10 volumes), 4-methylmorpholine (1.5 equivalents), and the carboxylic acid (3) symmetric anhydride (1.1 equivalent) is refluxed over 10 minutes to 2 hours.

(7) A mixture of Amine (2), dichloromethane (10 volumes), pyridine (1.5 equivalents), the mixed anhydride of the carboxylic acid (3) and methanesulfonic acid (1.1 equivalent) at between 0° C. and 35° C. over a 1 to 3 hours period.

(8) A mixture of Amine (2), dimethylformamide (5 volumes), dimethylaniline (1.3 equivalents), and the Vilsmeier reagent consisting from the carboxylic acid (3) and dimethylformamide (1.1 equivalent) is stirred at about 25° C. over 1 to 5 hours period.

(9) A mixture of Amine (2), ethyl acetate (10 volumes), pyridine (1.5 equivalents), and the mixed anhydride of diethyl hydrogen phosphate and the carboxylic acid (3) is stirred at between 0° C. and 10° C. over a 1 to 5 hours period.

(10) A mixture of Amine (2), ethyl acetate (7 volumes), dichloromethane (10 volumes), pyridine (2 equivalents), and the mixed anhydride of the carboxylic acid (3) and dichlorophosphoric acid (1.1 equivalent) is stirred over a 1 to 3 hours period at a temperature between 0° C. and 30° C.

(11) A mixture of Amine (2), lutidine (1.5 equivalents), dichloromethane (10 volumes), and the mixed anhydride of the carboxylic acid (3) and monochlorophosphoric acid dimethylamide is stirred over 1 to 4 hours at between 0° C. and 30° C.

(12) A mixture of Amine (2), carbonyldiimidazole (1.1 equivalent), tetrahydrofuran (10 volumes), dimethylacetamide (5 volumes), and the carboxylic acid (3) (1.1 equivalent) is stirred over a 1 to 5 hours period at between 0° C. and 35° C.

(13) A mixture of Amine (2), dichloromethane (10 volumes), dimethylformamide (5 volumes), N,N-dicyclohexylcarbodiimide (1.1 equivalent), picoline (1.2 equivalents), and the carboxylic acid (3) (1.1 equivalent) is refluxed over 5 hour.

(14) A mixture of Amine (2), dichloromethane (10 volumes), 2-ethoxy-1-ethoxycarbonyl-1,2-dihydroquinoline (1.1 equivalent), N,N'-dicyclohexylcarbodiimide (1.1 equivalent), pyridine (1.5 equivalents), and the carboxylic acid (3) (1.1 equivalent) is stirred over a 1 to 6 hours period at a temperature between 0° C. and 35° C.

(15) A mixture of Amine (2), dichloromethane (30 volumes), cyanuric chloride (1.1 equivalent), pyridine (4 equivalents), and the carboxylic acid (3) (1.1 equivalent) is stirred over a 30 minutes to 2 hours period at between −30° C. to 20° C.

(16) A mixture of Amine (2), dichloromethane (3 volumes), phosphorus oxychloride (1.1 equivalent), pyridine (1.5 equivalents), and the carboxylic acid (3) (1.1 equivalent) is stirred over 20 minutes to 2 hours at between −10° C. to 0° C.

(17) Amine (2) is treated with trimethylsilyl chloride to obtain the corresponding N-trimethylsilyl compound, and this is treated with phosphorus oxychloride (1.5 equivalents), the carboxylic acid (3) (1.2 equivalents), and pyridine (4 equivalents) in dichloromethane (5 weights) for 30 minutes to 2 hours at between 0° C. and room temperature.

(18) A mixture of Amine (2), dichloromethne (8 volumes), thionyl chloride (1.5 equivalents), pyridine (2.5 equivalents), and the carboxylic acid (3) (1.1 equiv.) is stirred over 1 to 5 hours at a temperature between −30° and 0° C.

(19) A mixture of Amine (2), dichloromethane (20 volumes), 1-hydroxybenzotriazole (2.1 equivalent), N,N'-dicyclohexylcarbodiimide (2.5 equivalents), and the carboxylic acid (3) (2 equivalents) is stirred at 0° C. to 20° C. over 1 to 15 hours.

(20) A mixture of Amine (2), dichloromethane (5 volumes), trifluoroacetic anhydride (1.5 equivalents), pyridine (3 equivalents), and the carboxylic acid (3) (1.5 equivalents) is stirred over 3 hours period at between 0° C. and 50° C.

(21) A mixture of Amine (2), dichloromethane (10 volumes), bromide of diethyl hydrogen phosphate (1.2 equivalents), 4-methylmorpholine (2.5 equivalents), and the carboxylic acid (3) (1.2 equivalents) is stirred over a 1 to 3 hours period at a temperature between 0° C. and 30° C.

(22) A mixture of Amine (2), ethyl acetate (10 volumes), di-2-pyridyl disulfide (1.1 equivalent), triphenylphosphine (1.1 equivalent), and the carboxylic acid (3) (1.1 equivalent) is stirred over a 5 hours period at between 10° and 50° C.

(23) A mixture of Amine (2), dichloromethane (3 volumes), 1,3,5-tripyridiniumtriazine trichloride (4 equivalents), and the carboxylic acid (3) (1.1 equivalent) is stirred over a 1 to 5 hours period at a temperature between −10° and 10° C.

(24) A mixture of Amine (2), tetrachloride (30 volumes), 4-methylmorpholine (1.5 equivalents), trisdiethylaminophosphine (1.1 equivalent), and the carboxylic acid (3) (1.1 equivalent) is kept at between −20° and 10° C. over 2 hours.

(25) A mixture of Amine (2), dioxane (10 volumes), N,N'-dicyclohexylcarbodiimide (2 equivalents), and phthalimide of the carboxylic acid (3) (2 equivalents) is stirred over a 2 to 8 hours period at a temperature between 10° and 50° C.

(26) A mixture of Amine (2), methyl isobutyl ketone (10 volumes), N,N'-dicyclohexylcarbodiimide (1.5 equivalents), and succinimide of the carboxylic acid (3) (1.5 equivalents) is stirred over a 2 to 9 hours period at between 0° and 40° C.

(27) A mixture of Amine (2), dichloromethane (20 volumes), pyridine (3 equivalents), N,N'-dicyclohexylcarbodiimide (3 equivalents), and 1-oxybenzotriazolyl ester of the carboxylic acid (3) (3 equivalents) is stirred over a 5 to 10 hours period at a temperature between 10° and 50° C.

(28) A mixture of Amine (2), chloroform (3 volumes), toluene (1 volume), picoline (2 equivalents), oxalyl chloride (1 equivalent), and the carboxylic acid (3) (1.1 equivalent) is stirred over a 10 minutes to 2 hours period at a temperature between −50° C. and 10° C.

EXAMPLE 2

(Heterocyclic thio introduction)

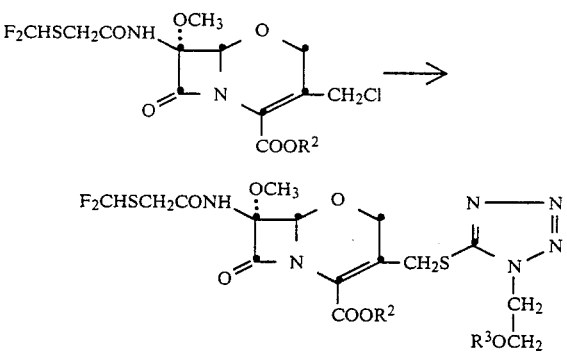

(1) ($R^3$=H, $R^2$=—CHPh$_2$)

To a solution of 7β-difluoromethylthioacetamido-7α-methoxy-3-chloromethyl-1-dethia-1-oxa-3-cephem-4-carboxylic acid diphenylmethyl ester (2 millimoles) in N,N-dimethylformamide (1 to 2 volumes) is added a solution of sodium 1-(2-hydroxyethyl)-1H-tetrazol-5-ylthiolate (1 to 2 equivalents) in N,N-dimethylformamide or methanol (1 to 2 volumes), and the mixture is stirred at a temperature between −10° C. and 50° C. over a 20 minutes to 5 hours period. The reaction mixture is washed with water, dried, and concentrated to dryness in vacuo. The residue is recrystallized from ethyl acetate to give 7β-difluoromethylthioacetamido-7α-methoxy-3-[1-(2-hydroxyethyl)-H-tetrazol-5-yl]thiomethyl-1-dethia-1-oxa-3-cephem-4-carboxylic acid diphenylmethyl ester.

Yield: 80 to 95%.

(2) In a manner similar to above, the reaction of tetrabutylammonium bromide (0.1 equivalent), 1-(2-hydroxyethyl)-5-tetrazol-5-ylthio (1.1 equivalent), sodium hydroxide (1.1 equivalent), and 7β-difluoromethylthioacetamido-7α-methoxy-3-chloromethyl-1-dethia-1-oxa-3-cephem-4-carboxylic acid diphenylmethyl ester in dichloromethane give the same product. Yield: 70 to 84%.

In a manner similar to above, the following compounds are produced from the corresponding 7β-difluoromethylthioacetamido-7α-methoxy-3-chloromethyl-1-dethia-1-oxa-3-cephem-4-carboxylate ester and the corresponding 1-(2-$R^3$-protected hydroxyethyl)-1H-tetrazol-5-ylthiol sodium salt:

(a) $R^2$=t—C$_4$H$_9$, $R^3$=t—C$_4$H$_9$,
(b) $R^2$=—CHPh$_2$, $R^3$=tetrahydropyran-2-yl,
(c) $R^2$=—CHPh$_2$, $R^3$=Cl$_2$CHCO—,
(d) $R^2$=—CHPh$_2$, $R^3$=PhCH$_2$OCO—,
(e) $R^2$=—CH$_2$C$_6$H$_4$OCH$_3$—p, $R^3$=p—CH$_3$C$_6$H$_4$CH$_2$OCO—,
(f) $R^2$=—CH$_2$CCl$_3$, $R^3$=H, The starting materials used here, 7β-difluoromethylthioacetamido-7α-methoxy-3-chloromethyl-1-dethia-1-oxa-3-cephem-4-carboxylic acid esters, can be produced as follows:

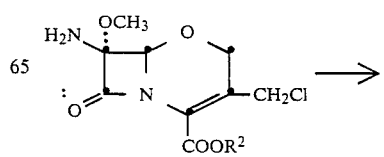

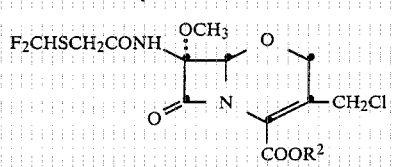

To a solution of 7β-amino-7α-methoxy-3-chloromethyl-1-dethia-1-oxa-3-cephem-4-carboxylic acid ester in dichloromethane (5 to 10 volumes) are added pyridine or picoline (2 to 10 equivalents) and difluoromethylthioacetyl chloride (1 to 1.5 equivalents), and the mixture is stirred under nitrogen over a 10 minutes to 2 hours period at a temperature between −30° C. and 10° C. The mixture is washed with aqueous sodium hydrogen carbonate and water, dried, and concentrated in vacuum. The residue is the corresponding ester of 7β-difluoromethylthioacetamido-7α-methoxy-3-chloromethyl-1-dethia-1-oxa-3-cephem-4-carboxylic acid. Yield: 50 to 93%.

EXAMPLE 3
(Deprotection)

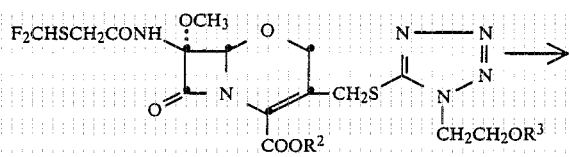

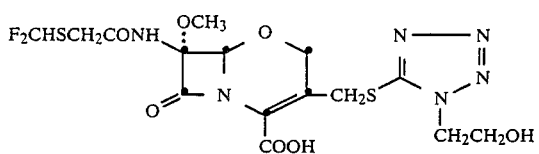

(1) Carboxy and hydroxy deprotections
(a) (R² = —CHPh₂, R³ = H):

To a solution of 7β-difluoromethylthioacetamido-7α-methoxy-3-[1-(2-hydroxyethyl)-1H-tetrazol-5-yl]thiomethyl-1-dethia-1-oxa-3-cephem-4-carboxylic acid diphenylmethyl ester (1 equivalent) in dichloromethane (5 volumes) are added anisole (0 to 10 equivalents) and titanium tetrachloride or aluminum chloride (1 to 5 equivalents), and the mixture is stirred over a 30 minutes to 6 hours period at a temperature between −45° C. and 10° C. The reaction mixture is washed with diluted hydrochloric acid and water, dried, and concentrated in vacuum. The acid part is collected and crystallized from ethyl acetate, acetone—dichloromethane, or methanol—ether to give 7β-difluoromethylthioacetamido-7α-methoxy-3-[1-(2-hydroxyethyl)-1H-tetrazol-5-yl]thiomethyl-1-dethia-1-oxa-3-cephem-4-carboxylic acid. Yield: 95%.

(b) (R² = —CHPh₂, R³ = H)

In place of aluminum chloride of preceding (a), trifluoroacetic acid (0.3 to 3 weights) is used to give the same compound in nearly quantitative yield.

(c) Substituting dichloromethane (2 to 5 weights) and titanium tetrachloride or aluminum chloride with dichloromethane-nitromethane (5 to 1:1) mixture (12 weights) and tin chloride respectively, the reaction of above (a or b) is repeated to obtain the same product in 85 to 98% yield.

(d) Under the same condition as in (a) to (c) above, the same compounds are produced from the compounds of the following partial structure.
  (i) R² = —CHPh₂, R³ = PhCH₂OCO—
  (ii) R² = —CH₂C₆H₄OCH₃—p, R³ = p—CH₃C₆H₄CH₂OCO—
  (iii) R² = t—C₄H₉, R³ = t—C₄H₉—
  (iv) R² = —CHPh₂, R³ = tetrahydropyran-2-yl
  (v) R² = —CHPh₂, R³ = —Si(CH₃)₂t—C₄H₉,
(2) Removing tetrahydropyranyl

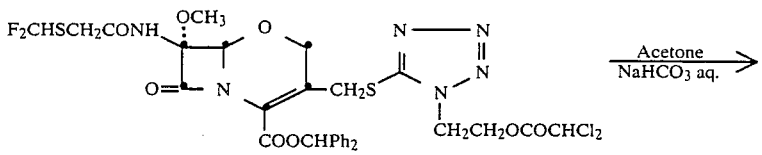

To a solution of 7β-difluoromethylthioacetamido-7α-methoxy-3-[1-(tetrahydropyran-2-yloxy)ethyl]-1H-tetrazol-5-yl]thiomethyl-1-dethia-1-oxa-3-cephem-4-carboxylic acid diphenylmethyl ester (2 millimoles) in methanol (2 ml) is added 1 N-hydrochloric acid (0.1 ml), and the mixture is kept at room temperature over a 1 to 2 hours period. The reaction mixture is neutralized with aqueous sodium hydrogen carbonate and concentrated. The residue is recrystallized from a mixture of acetone and benzene to give a diphenylmethyl ester identical with the product of Example 2(1).

(3) Removing dichloroacetyl

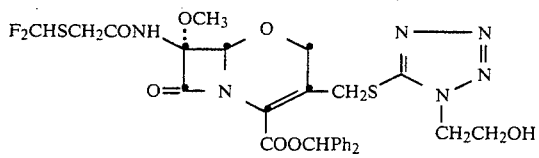

To a solution of 7β-difluoromethylthioacetamido-7α-methoxy-3-[1-(2-dichloroacetoxyethyl)-1H-tetrazol-5-yl]thiomethyl-1-dethia-1-oxa-3-cephem-4-carboxylic acid diphenylmethyl ester (4 millimoles) in acetone (10 ml) is added aqueous 1 N-sodium hydrogen carbonate (1 ml), and the mixture is refluxed for 30 minutes. The reaction mixture is neutralized with acetic acid and concentrated to remove acetone. The residue is extracted with ethyl acetate. The extract is washed with water, dried, and concentrated to give a diphenylmethyl ester identical with the product of Example 2(1). Yield: 76%.

EXAMPLE 4

(Salt formation)

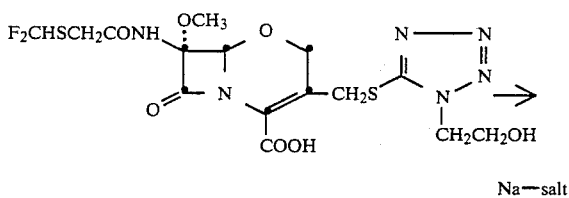

(1) To a solution of 7β-difluoromethylthioacetamido-7α-methoxy-3-[1-(2-hydroxyethyl)-1H-tetrazol-5-yl]thiomethyl-1-dethia-1-oxa-3-cephem-4-carboxylic acid (2 millimoles) in ethyl acetate is added a 3 M-solution of potassium 2-ethylhexanoate (1 to 1.5 equivalents) in methanol, and the mixture is stirred for 0.5 hours. The reaction mixture is concentrated in vacuum. The residue is stirred in ether to give the corresponding potassium salt. Yield: 81%.

(2) The starting carboxylic acid of above (1) (1 equivalent is dissolved in aqueous 1 M-sodium hydrogen carbonate (1 equivalent) and conventionally lyophilized. This salt is given intravenously as injection in water or orally as suspension in glycerin monooctanoate at a daily dose of 2 g to treat an infection caused by sensitive Staphylococcus aureus.

MIC: *Escherichia coli* = <0.1 μg/ml.

EXAMPLE 5

(Pharmaceutically acceptable ester)

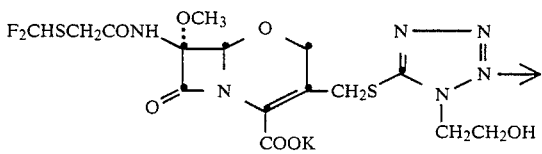

-continued

F₂CHSCH₂CONH, OCH₃, structure with COOPOM and CH₂CH₂OH (1) To a solution of 7β-difluoromethylthioacetamido-7α-methoxy-3-[1-(2-hydroxyethyl)-1H-tetrazol-5-yl]thiomethyl-1-dethia-1-oxa-3-cephem-4-carboxylic acid potassium salt (1 millimole) in N,N-dimethylformamide (2 to 5 weights) is added iodomethyl pivalate (1 to 2 equivalents) under ice cooling, and the mixture is stirred for ¼ to 2 hours. The reaction mixture is diluted with ethyl acetate, washed with iced aqueous sodium hydrogen carbonate, dried, and concentrated in vacuum. The residue is recrystallized from ethyl acetate to give 7β-difluoromethylthioacetamido-7α-methoxy-3-[1-(2-hydroxyethyl)-1H-tetrazol-5-yl]thiomethyl-1-dethia-1-oxa-3-cephem-4-carboxylic acid pivaloyloxymethyl ester. Yield: 67%.

(2) Substituting the potassium salt with the corresponding sodium salt, the reaction of above (1) is repeated to afford the same product. Yield: 72%.

(3) Substituting iodomethyl pivalate with iodomethyl acetate or iodoethyl ethoxyformate, the reaction of above (1) is repeated to afford the corresponding acetoxymethyl ester or ethoxycarbonyloxyethyl ester (Polar and nonpolar isomers).

(4) In a manner similar to above (1), phthalidyl bromide is reacted on the potassium salt of the carboxylic acid to afford two stereoisomers at the ester group of the corresponding phthalidyl ester (Polar and nonpolar isomers).

(5) 5-Indanol and methanesulfonyl chloride are reacted on the carboxylic acid in the presence of pyridine at −10° C. for 90 minutes in dichloromethane to obtain the corresponding indanyl ester.

(6) Pivaloyloxymethyl ester of (1) (250 mg), corn starch (150 mg), and magnesium stearate (5 mg) are mixed, granulated, and filled in a gelatine capsule. One to three of this capsule is orally administered thrice a day to a patient infected by sensitive *Staphylococcus aureus* to treat the infection.

(7) Similarly, the acetoxymethyl ester or ethoxycarbonyloxyethyl ester of (3) above is encapsulated and administered orally to treat the same infection.

EXAMPLE 6
(Methoxylation)

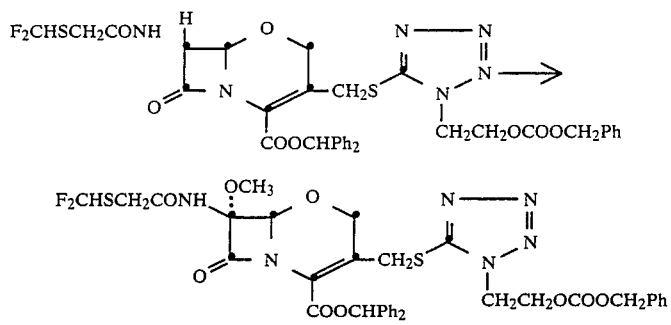

To a solution of 7α-difluoromethylthioacetamido-3-[1-(2-benzyloxycarbonyloxyethyl)-1H-tetrazol-5-yl]thiomethyl-1-dethia-1-oxa-3-cephem-4-carboxylic acid diphenylmethyl ester (5 g) in dichloromethane (10 ml) are added pyridine (1.1 equivalent) and chlorine (2 equivalents) under ice cooling. A solution of lithium methoxide (3 equivalents) in methanol is added to the mixture cooled at −50° C., and the mixed solution is let stand for 2 hours. The reaction mixture is neutralized with acetic acid, washed with water, dried, and concentrated in vacuum to afford 7β-difluoromethylthioacetamido-7α-methoxy-3-[1-(2-benzyloxycarbonyloxyethyl)-1H-tetrazol-5-yl]thiomethyl-1-dethia-1-oxa-3-cephem-4-carboxylic acid diphenylmethyl ester (3.5 g).

EXAMPLE 7
(Protection)

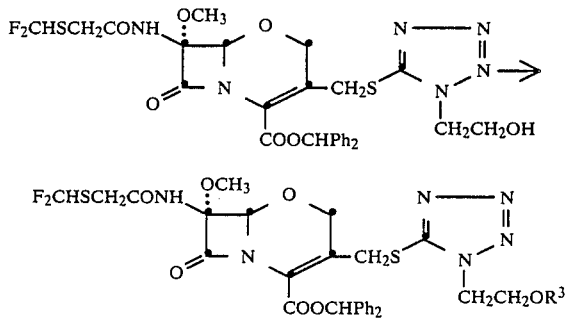

(1) ($R^3$=benzyloxycarbonyl)

To a suspension of 7β-difluoromethylthioacetamido-7α-methoxy-3-[1-(2-hydroxyethyl)-1H-tetrazol-5-yl]thiomethyl-1-dethia-1-oxa-3-cephem-4-carboxylic acid diphenylmethyl ester in dichloromethane (40 volumes) cooled at 0° C. is added pyridine (5.6 equivalents) and benzyl chloroformate (1.5 equivalents). The mixture is stirred at 0° C. for 6 hours and at 25° C. for 3 hours. Usual work up of the reaction mixture gives 7β-difluoromethylthioacetamido-7α-methoxy-3-[1-(2-benzyloxycarbonyloxyethyl)-1H-tetrazol-5-yl]thiomethyl-1-dethia-1-oxa-3-cephem-4-carboxylic acid diphenylmethyl ester. Yield: 95%. This product is the same to that of Example 1 (2), (f).

(2) ($R^3$=t-butyldimethylsilyl)

To a solution of 7β-difluoromethylthioacetamido-7α-methoxy-3-[1-(2-hydroxyethyl)-1H-tetrazol-5-yl]thiomethyl-1-dethia-1-oxa-3-cephem-4-carboxylic acid diphenylmethyl ester in N,N-dimethylformamide (3 volumes) cooled at 0° C. is added 4-methylmorpholine (1.4 equivalents) and t-butyldimethylsilyl chloride (1.4 equivalents). The mixture is stirred at 0° C. for 1.5 hours, diluted with brine, and extracted with ethyl acetate. The extract is washed with brine, dried over magnesium sulfate, and concentrated to give oily material. This is purified by silica gel chromatography to give 7β-difluoromethylthioacetamido-7α-methoxy-3-[1-(2-t-butyldimethylsilyloxyethyl)-1H-tetrazol-5-yl]thiomethyl-1-dethia-1-oxa-3-cephem-4-carboxylic acid diphenylmethyl ester. Yield: 95%. This product is identical with that of Example 1 (2), (j).

Similarly, the products (a) to (j) of Example 1 (2) can be prepared according to a conventional manner in the art.

EXAMPLE 8 ($R^1$=2-hydroxypropyl)

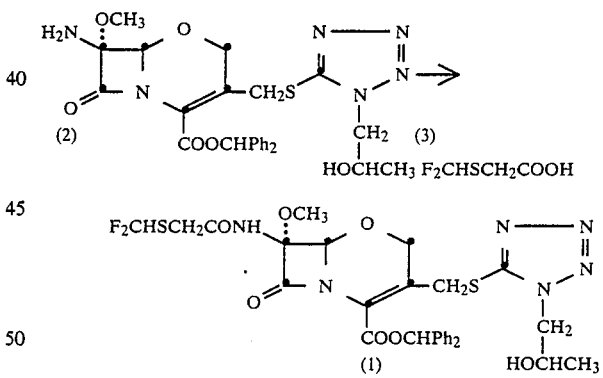

(1) Amidation

Substituting the 7β-amino-7α-methoxy-3-[1-(2-hydroxyethyl)-1H-tetrazol-5-yl]thiomethyl-1-dethia-1-oxa-3-cephem-4-carboxylic acid diphenylmethyl ester with 7β-amino-7α-methoxy-3-[1-(2-hydroxypropyl)-1H-tetrazol-5-yl]-thiomethyl-1-dethia-1-oxa-3-cephem-4-carboxylic acid diphenylmethyl ester, Example 1 (2) is repeated to afford 7β-difluoromethylthioacetamido-7α-methoxy-3-[1-(2-hydroxypropyl)-1H-tetrazol-5-yl]thiomethyl-1-dethia-1-oxa-3-cephem-4-carboxylic acid diphenylmethyl ester.

The Amine (2) is treated with the side chain carboxylic acid (3) or its reactive derivative under a condition of Example 1, (3), (1) to (28) to give a product of Example 8(1).

(2) HetS introduction

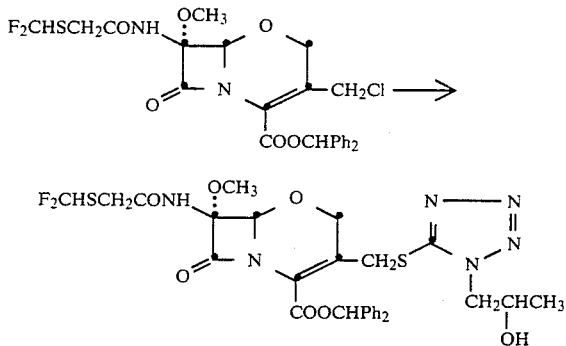

Substituting 1-(2-hydroxyethyl)-1H-tetrazol-5-ylthiol sodium salt with 1-(2-hydroxypropyl)-1H-tetrazol-5-ylthiol sodium salt, Example 2, (1) is repeated to give the product identical with that of Example 8(1).

(3) Deesterification

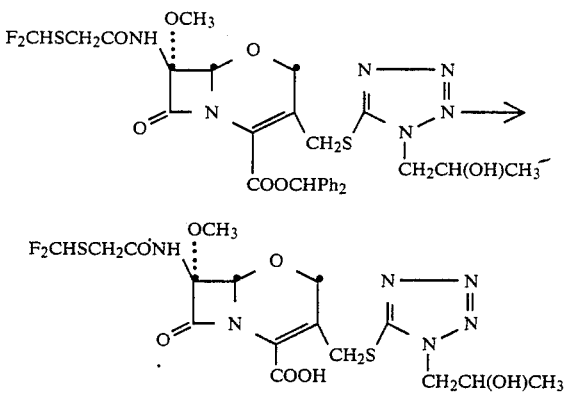

Substituting 7β-difluoromethylthioacetamido-7α-methoxy-3-[1-(hydroxyethyl)-1H-tetrazol-5-yl]thiomethyl-1-dethia-1-oxa-3-cephem-4-carboxylic acid diphenylmethyl ester with 7β-difluoromethylthioacetamido-7α-methoxy-3-[1-(2-hydroxypropyl-propyl)-1H-tetrazol-5-yl]thiomethyl-1-dethia-1-oxa-3-cephem-4-carboxylic acid diphenylmethyl ester, Example 3, (1) (a) is repeated to give 7β-difluoromethylthioacetamido-7α-methoxy-3-[1-(2-hydroxypropyl)-1H-tetrazol-5-yl]thiomethyl-1-dethia-1-oxa-3-cephem-4-carboxylic acid.

(4) (Salt formation and pivaloyloxymethyl ester)

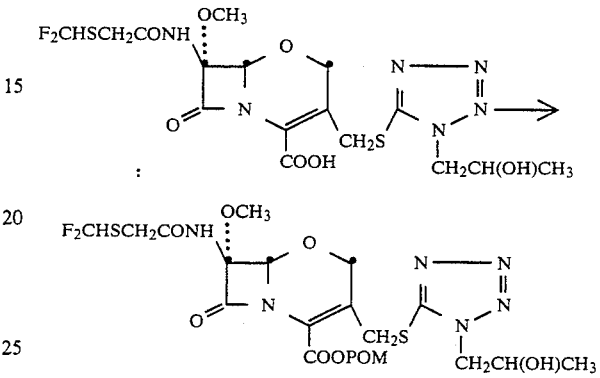

Substituting 7β-difluoromethylthioacetamido-7α-methoxy-3-[1-(2-hydroxyethyl)-1H-tetrazol-5-yl]thiomethyl-1-dethia-1-oxa-3-cephem-4-carboxylic acid with 7β-difluoromethylthioacetamido-7α-methoxy-3-[1-(2-hydroxypropyl)-1H-tetrazol-5-yl]thiomethyl-1-dethia-1-oxa-3-cephem-4-carboxylic acid, Example 4 is repeated to give 7β-difluoromethylthioacetamido-7α-methoxy-3-[1-(2-hydroxypropyl)-1H-tetrazol-5-yl]thiomethyl-1-dethia-1-oxa-3-cephem-4-carboxylic acid potassium salt, and this product is esterified by the method of Example 5 to afford the corresponding pivaloyloxymethyl ester.

TABLE 1-1

| No. | $R^2$ | $R^3$ | IR(CHCl$_3$) cm$^{-1}$ | NMR(CDCl$_3$) ppm. |
|---|---|---|---|---|
| 1 | H | H | 3440, 1780, 1790, 1710, 1680(KBr). | (CD$_3$SOCD$_3$): 3.42(s, 3H), 3.63(s, 2H), 3.75 (t, J = 6Hz, 2H), 4.21(s, 2H), 4.33(t, J = 6 Hz, 2H), 4.53(s, 2H), 5.07(s, 1H), 7.03(t, J = 56Hz, 1H), 9.22(s, 1H). |
| 2 | Na | H | 3400, 1766, 1687, 1610 (KBr). | (D$_2$O): 4.00(s, 3H), 4.18(s, 2H), 4.47(t, J = 6Hz, 2H), 4.57, 4,74(ABq, J = 7.5Hz, 2H), 5.01(t, J = 6Hz, 2H), 5.01(s, 2H), 5.13(s, 1H), 7.58(t, J = 56Hz, 1H). |
| 3 | CH$_2$CCl$_3$ | H | 3390, 1792, 1738, 1696. | (CDCl$_3$ + CD$_3$SOCD$_3$(1:1)): 3.46(s, 3H), 3.59 (s, 2H), 3.83 (t, J = 5.8Hz, 2H), 4.2–4.9 (m, 8H), 5.01(s, 1H), 7.15(t, J = 56Hz, 1H), 9.13(s, 1H). |
| 4 | t-C$_4$H$_9$ | t-C$_4$H$_9$ | 1775, 1770. | |
| 5 | PMB | Tbz | 3300, 1792, 1716. | |
| 6 | PMB | Cbz | 1790, 1755, 1709. | |

Tbz = p-methylbenzyloxycarbonyl.

TABLE 1-2

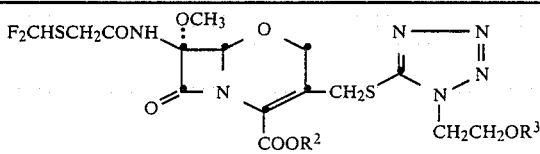

| No. | R² | R³ | IR(CHCl₃) cm⁻¹ | NMR(CDCl₃) ppm. |
|---|---|---|---|---|
| 7 | CHPh₂ | H | | mp. 170–172° C. |
| 8 | CHPh₂ | Cl₂CHCO— | 1780, 1721. | |
| 9 | CHPh₂ | PhCH₂OCO— | 3375, 1785, 1746, 1703, 1624, 1391. | 3.53 (s, 5H), 4.19 (s, 2H), 4.37 (s, 4H), 4.57 (s, 2H), 5.03 (s, 1H), 5.07 (s, 2H), 6.89 (s, 1H), 6.89 (t, J = 56 Hz, 1H), 7.07–7.75 (m, 11H). mp. 134–136° C. |
| 10 | CHPh₂ | MePhCH₂OCO— | 3375, 1787, 1746, 1708, 1630, 1398, 1262, 1078. | 2.30 (s, 3H), 3.53 (s, 5H), 4.20 (s, 2H), 4.38 (s, 4H), 4.57 (s, 2H), 5.02 (s, 3H), 6.87 (s, 1H), 6.87 (t, J = 56 Hz, 1H), 7.03–7.63 (m, 15H). |
| 11 | CHPh₂ | THP | 3400, 1785, 1705. | |
| 12 | CHPh₂ | Si(CH₃)₂t-C₄H₉ | 3365, 1784, 1720, 1700, 1624, 1600, 1390, 1250, 1123, 1066. | 0.10 (s, 3H), 0.17 (s, 3H), 0.78 (s, 9H), 3.53 (s, 5H), 3.90 (t, J = 5.5 Hz, 2H), 4.05–4.38 (m, 4H), 4.60 (br s, 2H), 5.03 (s, 1H), 6.90 (s, 1H), 6.90 (t, J = 56.4 Hz, 1H), 7.20–7.6 (m, 11H). |

TABLE 1-3

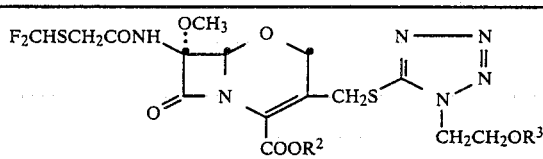

| No. | R² | R³ | IR(CHCl₃) cm.⁻¹ | NMR(CDCl₃) ppm. |
|---|---|---|---|---|
| 13 | AOM | H | 3400, 1790, 1780, 1740, 1700, 1632. | (CDCl₃ + CD₃SOCD₃(2:1): 2.13(s, 3H), 3.51 (s, 3H), 3.56(s, 2H), 3.93(t, J = 6Hz, 2H), 4.29(t, J = 6Hz, 2H), 4.35(s, 2H), 4.61(s, 2H), 5.06(s, 1H), 5.83, 5.98(q, J = 6Hz, 2H), 7.09(t, J = 56Hz, 1H), 9.11(s, 1H). |
| 14 | POM | H | 3392, 1790, 1751, 1700, 1632. | 1.22(s, 9H), 3.50(s, 3H), 3.55(s, 2H), 4.05(t, J = 4.5Hz, 2H), 4.21(s, 2H), 4.37 (t, J = 4.5Hz, 2H), 4.57(s, 2H), 5.03(s, 1H), 5.82, 5.95 (q, J = 6Hz, 2H), 6.92(t, J = 56 Hz, 1H), 7.34(s, 1H). |
| 15 | POM | H | 3392, 1792, 1756, 1700, 1631. | 1.13(s, 3H), 1.21(s, 3H), 2.57, 2.66(q, J = 6Hz, 1H), 3.53(s, 3H), 3.56(s, 2H), 4.03(t, 4.5Hz, 2H), 4.23(s, 2H), 4.37(t, J = 4.5Hz, 2H), 4.59(s, 2H), 5.04(s, 1H), 5.83, 5.95(ABq, J = 6Hz, 2H), 6.93(t, J = 56 Hz, 1H), 7.43(s, 1H). |

TABLE 1-4

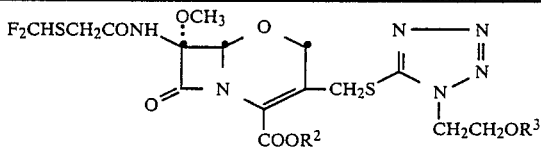

| No. | R² | R³ | IR(CHCl₃) cm⁻¹ | NMR(CDCl₃) ppm. |
|---|---|---|---|---|
| 16 | Phthalidyl (Polar isomer) | H | 3380, 1794, 1736, 1700. | (CDCl₃ + CD₃SOCD₃(1:1)): 3.39(s, 3H), 3.53 (s, 2H), 3.7–4.5(m, 6H), 4.60(s, 2H), 5.01(s, 1H), 7.08(t, J = 56 Hz, 1H), 7.55 (s, 1H), 7.6–8.0 (m, 5H), 9.15(s, 1H). |
| 17 | (Nonpolar isomer) | | 3381, 1795, 1739, 1705. | (CDCl₃ + CD₃SOCD₃(1:1)): 3.41(s, 3H), 3.56 (s, 2H), 3.93(t, J = 5.8Hz, 2H), 4.30(s, 2H), 4.36(t, J = 5.8 Hz, 2H), 4.65(s, 2H), 5.01(s, 1H), 7.08(t, J = 56 Hz, 1H), 7.46 (s, 1H), 7.55–8.0(m, 5H), 9.06(s, 1H). |
| 18 | ECE (Polar isomer) | H | 3400, 1793, 1765, 1702. | 1.29(t, J = 7.5Hz, 3H), 1.60(d, J = 6Hz, 3H), 3.51(s, 3H), 3.69(s, 2H), 3.8–4.5(m, 8H), 4.60(s, 2H), 5.06(s, 1H), 6.83, 6.95 |

TABLE 1-4-continued

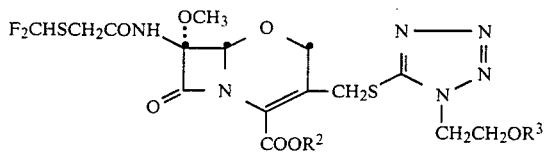

| No. | R² | R³ | IR(CHCl₃) cm⁻¹ | NMR(CDCl₃) ppm. |
|---|---|---|---|---|
| | | | | (ABq, J = 5.6Hz, 1H), 6.96(t, J = 56Hz, 1H), 7.55 (s, 1H). |

TABLE 1-5

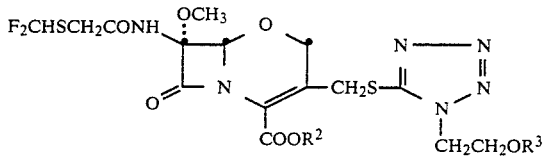

| No. | R² | R³ | IR(CHCl₃) cm⁻¹ | NMR(CDCl₃) ppm. |
|---|---|---|---|---|
| 19 | (Nonpolar isomer | | 3395, 1790, 1760, 1702. | 1.30 (t, J=7.5Hz, 3H), 1.60 (d, J=6Hz, 3H), 3.53 (s, 3H), 3.60 (s, 2H), 3.9–4.5 (m, 8H), 4.63 (s, 2H), 5.06 (s, 1H), 6.83, 6.95 (ABq, J=5.6Hz, 1H), 6.96 (t, J=56Hz, 1H), 7.53 (s, 1H). |
| 20 | indanyl | H | 3400, 1790, 1731, 1700. | 1.9–2.3 (m, 2H), 2.75–3.15 (m, 4H), 3.53 (s, 5H), 4.02 (br s, 2H), 4.2–4.5 (m, 4H), 5.12 (s, 1H), 6.91 (t, J=56Hz, 1H), 6.95–7.3 (m, 3H), 7.63 (s, 1H). |
| 21 | 4-carboxy-phthalidyl dl-mixture | H | | (CD₃COCD₃): 3.11 (s, 3H), 3.42 (s, 2H), 3.71 (t, J=5.8Hz, 2H), 3.8–4.4 (m, 4H), 4.46 (s, 2H), 4.80 (s, 1H), 6.96 (t, J=56Hz, 1H), 7.4–8.4 (m, 5H). |

TABLE 1-6

Starting amines

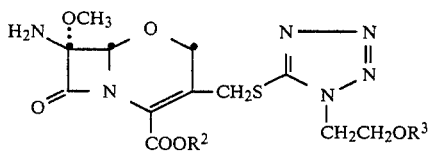

| No. | R² | R³ | IR(CHCl₃) cm⁻¹ | NMR(CDCl₃) ppm. |
|---|---|---|---|---|
| 22 | CHPh₂ | Cbz | 3340, 1785, 1758, 1720, | mp. 112.5–114.5° C. 3.13 (br s, 2H), 3.44 (s, 3H), 4.22 (s, 2H), 4.49 (s, 4H), 4.63 (s, 2H), 4.89 (s, 1H), 5.05 (s, 2H), 6.83 (s, 1H), 7.1–7.8 (m, 15H). |
| 23 | CHPh₂ | Tbz | 3410, 3340, 1790, 1754, 1721(Nujol). | mp. 135–138.5° C. 2.17 (br s, 2H), 2.31 (s, 3H), 3.50 (s, 3H), 4.24 (s, 4H), 4.41 (s, 4H), 4.61 (ABq, 2H), 4.84 (s, 1H), 5.05 (s, 2H), 6.92 (s, 1H), 7.05–7.7 (m, 14H). |

TABLE 2

(R¹ = 2-oxypropyl)

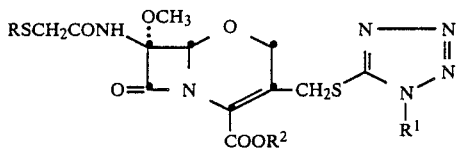

| No. | R² | R³ | IR(CHCl₃) cm$^{-1}$ | NMR(CDCl₃) ppm. |
|---|---|---|---|---|
| 24 | H | H | 1762, 1680, 1605(Nujol). | |
| 25 | POM | H | 3380, 3130, 1792, 1751, 1700. | |
| 26 | CHPh₂ | H | 3370, 1785, 1715, 1703. | |
| 27 | CHPh₂ | PHCH₂OCO— | 3498, 3282, 1768, 1708, 1673, 1626. | |

What we claim is:

1. A 7β-(fluorinated methylthio)acetamido-7α-methoxy-3-[1-(2-hydroxyalkyl)-1H-tetrazol-5-yl]thiomethyl-1-dethia-1-oxa-3-cephem-4-carboxylic acid derivative represented by the following formula:

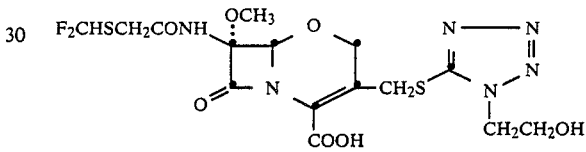

wherein

R is FCH₂— or F₂CH—;

R¹ is optionally protected 2-hydroxyalkyl; and

R² is hydrogen, a light metal atom, or a carboxy-protecting group.

2. A compound as claimed in claim 1 wherein R is difluoromethyl.

3. A compound as claimed in claim 1 wherein R¹ is hydroxyethyl or 2-hydroxypropyl.

4. A compound as claimed in claim 1, wherein R¹ is 2-hydroxyethyl protected by benzyloxycarbonyl, t-butoxycarbonyl, t-butyl, t-butyldimethylsilyl, dichloroacetyl, p-methylbenzyloxycarbonyl, or tetrahydropyran-2-yl.

5. A compound as claimed in claim 1 wherein R² is hydrogen, sodium, potassium, calcium, acetoxymethyl, diphenylmethyl, or 1-(ethoxycarbonyloxy)ethyl, indanyl, p-methoxybenzyl, phthalidyl, or pivaloyloxymethyl.

6. A compound as claimed in claim 1 wherein R is difluoromethyl, R¹ is hydroxyethyl, and R² is hydrogen; R is difluoromethyl, R¹ is hydroxyethyl, and R² is sodium; R is difluoromethyl, R¹ is hydroxyethyl, and R² is acetoxymethyl; R is difluoromethyl, R¹ is hydroxyethyl, and R² is 1-(ethoxycarbonyloxy)ethyl; R is difluoromethyl, R¹ is hydroxyethyl, and R² is indanyl; R is difluoromethyl, R¹ is hydroxyethyl, and R² is phthalidyl; R is difluoromethyl, R¹ is hydroxyethyl, and R² is pivaloyloxymethyl; R is difluoromethyl, R¹ is hydroxypropyl, and R² is hydrogen; R is difluoromethyl, R¹ is hydroxypropyl, and R² is sodium; or R is difluoromethyl, R¹ is hydroxypropyl, and R² is pivaloyloxymethyl.

7. A compound according to claim 1 of the formula

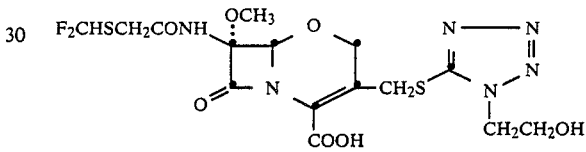

or the sodium salt thereof.

8. An antibacterial composition comprising an antibacterially effective amount of the compound as claimed in claim 1 and conventional carrier.

9. A method for combating bacteria which comprises bringing an antibacterially effective amount of the compound as claimed in claim 1 into contact with the bacteria.

* * * * *